(12) United States Patent
Marx et al.

(10) Patent No.: US 8,252,738 B2
(45) Date of Patent: *Aug. 28, 2012

(54) METHOD FOR CHANGING CELL PHENOTYPE USING LIM MINERALIZATION PROTEINS

(75) Inventors: Jeffrey C. Marx, Germantown, TN (US); William F. McKay, Memphis, TN (US); Susan J. Drapeau, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 239 days.

This patent is subject to a terminal disclaimer.

(21) Appl. No.: 11/875,267

(22) Filed: Oct. 19, 2007

(65) Prior Publication Data

US 2009/0105117 A1 Apr. 23, 2009

Related U.S. Application Data

(63) Continuation-in-part of application No. 11/705,942, filed on Feb. 14, 2007, and a continuation-in-part of application No. 10/292,951, filed on Nov. 13, 2002, now Pat. No. 7,923,250, application No. 11/875,267, which is a continuation-in-part of application No. 10/806,915, filed on Mar. 23, 2004, now Pat. No. 7,892,532, which is a continuation-in-part of application No. 09/959,578, filed as application No. PCT/US00/11664 on Apr. 28, 2000, now Pat. No. 7,045,614, application No. 11/875,267, which is a continuation-in-part of application No. 10/399,830, filed as application No. PCT/US01/46044 on Oct. 24, 2001, now Pat. No. 8,226,729.

(60) Provisional application No. 60/331,321, filed on Nov. 14, 2001, provisional application No. 60/456,551, filed on Mar. 24, 2003, provisional application No. 60/132,021, filed on Apr. 30, 1999, provisional application No. 60/242,794, filed on Oct. 24, 2000.

(51) Int. Cl.
*A61K 38/00* (2006.01)
*A61K 38/16* (2006.01)
*A61K 38/17* (2006.01)
*A61K 38/18* (2006.01)
*C12N 15/00* (2006.01)
*C12N 15/12* (2006.01)

(52) U.S. Cl. ...... 514/1.1; 424/93.21; 424/422; 424/423; 514/44 R

(58) Field of Classification Search .................. None
See application file for complete search history.

(56) References Cited

U.S. PATENT DOCUMENTS

| 6,300,127 | B1 | 10/2001 | Hair et al. |
| 2005/0234425 | A1* | 10/2005 | Miller et al. ............. 604/508 |
| 2007/0027081 | A1 | 2/2007 | Marx et al. |

FOREIGN PATENT DOCUMENTS

| WO | WO 99/06563 | * | 2/1999 |
| WO | 2005111058 A1 | | 11/2005 |
| WO | WO 2005/111058 A1 | * | 11/2005 |

OTHER PUBLICATIONS

Boden et al., 1998, Endocrinology 139:5125-5134.*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Liu et al., 2002, J. Bone and Mineral Res. 17: 406-414.*
Yoon et al., 2005, The Spine J. 5: 280S-286S.*
Boden, et al., LMP-1, A LIM-Domain Protein, Mediates BMP-6 Effects on Bone Formation, Endocrinology 139 (12):5125-5134 (1998).
David, et al., LIM domains: multiple roles as adapters and functional modifiers in protein interactions, Trends Genet. 1998; 14:156-62.
St. Yoon, et al., ISSLS Prize Winner: LMP-1 Upregulates Intervertebral Disc Cell Production of Proteoglycans and BMPs In Vitro and In Vivo, Spine vol. 29, No. 23, pp. 2603-2611 (2004).
Hogan, Bone morphogenetic proteins: multifunctional regulators of vertebrate development, Genes & Development, 10,1580-94 (1996) Cold Spring Harbor Laboratory Press, ISSN 0890-9369/96.
D.M. Kingsley, What do BMPs do in mammals? Clues from the mouse short-ear mutation,Trends Genet., (1994) vol. 10 No. 1, pp. 16-21.
K.W. Liechty et al., Human Mesenchymal Stem Ceils Engraft and Demonstrate Site-specific Differentiation After in Utero Transplantation in Sheep, Nature Medicine, vol. 6 No. 11, pp. 1282-1286 (2000).
D.J. Prockop, Marrow Stromal Cells as Stem Cells for Nonhematopoietic Tissues, 276 Science 71-4 (1997).
M.F. Pittenger et al., Multilineage Potential of Adult Human Mesenchymal Stem Cells, 284 Science 143-7 (1999).
P. Bianco et al., Bone Marrow Stromal Stem Cells: Nature, Biology, and Potential Applications, 19 Stem Cells 180-92 (2001).
N. Adachi et al., Muscle Derived, Cell Based Ex Vivo Gene Therapy for Treatment of Full Thickness Articular Cartilage Defects, 29 J. Rheumatoogy. 1920-30-(2002).

(Continued)

*Primary Examiner* — Elizabeth C Kemmerer

(57) ABSTRACT

Methods of changing a phenotype of a cell are provided. The methods comprise increasing an amount of an amino acid sequence which is at least 70% identical to an amino acid sequence encoding an LMP protein or a fragment thereof in a cell. The cells may be contacted by either a composition comprising a nucleic acid sequence encoding the amino acid sequence which is at least 70% identical to the amino acid sequence encoding an LMP or its fragment or by a composition comprising acid sequence which is at least 70% identical to the amino acid sequence encoding an LMP or its fragment or any combination thereof. The cells may be contacted either in vivo or ex-vivo.

19 Claims, No Drawings

OTHER PUBLICATIONS

Y. Gafni et al., Stem Cells as Vehicles for Orthopedic Gene Therapy, 11 Gene Therapy 417-26 (2004).

Boden, et al., Glucocorticoid-Induced Differentiation of Fetal Rat Calvarial Osteoblasts Is Mediated by Bone Morphogenetic Protein-6, Endocrinology, 138, 2820-8 (1997).

Wells, Additivity of Mutational Effects in Proteins, 1990, Biochemistry vol. 29 No. 37:8509-8517.

Ngo et al., 1994, Computational Complexity, Protein Structure Prediction, and the Levinthal Paradox,The Protein Folding Problem and Tertiary Structure Prediction, Merz et al., eds., Birkhauser, Boston, pp. 492-495.

* cited by examiner

SEQUENCE LISTING

<160> NUMBER OF SEQ ID NOS: 18

<210> SEQ ID NO 1
<211> LENGTH: 457
<212> TYPE: PRT
<213> ORGANISM: Homo sapiens

<400> SEQUENCE: 1

Met Asp Ser Phe Lys Val Val Leu Glu Gly Pro Ala Pro Trp Gly Phe
1               5                   10                  15

```
Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
             35                  40                  45

Trp Val Leu Ser Ile Asp Gly Glu Asn Ala Gly Ser Leu Thr His Ile
 50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
                100                 105                 110

Asn Lys Thr Ala Arg Pro Phe Gly Ala Pro Pro Ala Asp Ser Ala
                115                 120                 125

Pro Gln Gln Asn Gly Gln Pro Leu Arg Pro Leu Val Pro Asp Ala Ser
        130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                    165                 170                 175

Glu Phe Met Gln Asp Pro Asp Glu Glu His Leu Lys Lys Ser Ser Gln
                180                 185                 190

Val Pro Arg Thr Glu Ala Pro Ala Pro Ala Ser Ser Thr Pro Gln Glu
            195                 200                 205

Pro Trp Pro Gly Pro Thr Ala Pro Ser Pro Thr Ser Arg Pro Pro Trp
        210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
                340                 345                 350

Met His Ala Leu Lys Met Thr Trp His Val His Cys Phe Thr Cys Ala
        355                 360                 365

Ala Cys Lys Thr Pro Ile Arg Asn Arg Ala Phe Tyr Met Glu Glu Gly
    370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
```

```
                    435                 440                 445
Cys Lys Ser His Ala Phe Ser His Val
    450                 455

<210> SEQ ID NO 2
<211> LENGTH: 423
<212> TYPE: PRT
<213> ORGANISM: Homo sapiens

<400> SEQUENCE: 2

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Val Gln Thr
                85                  90                  95

Pro Asp Lys Gln Pro Leu Arg Pro Leu Val Pro Asp Ala Ser Lys Gln
            100                 105                 110

Arg Leu Met Glu Asn Thr Glu Asp Trp Arg Pro Arg Pro Gly Thr Gly
        115                 120                 125

Gln Ser Arg Ser Phe Arg Ile Leu Ala His Leu Thr Gly Thr Glu Phe
    130                 135                 140

Met Gln Asp Pro Asp Glu His Leu Lys Lys Ser Ser Gln Val Pro Arg
145                 150                 155                 160

Arg Thr Glu Ala Pro Ala Pro Ala Ser Ser Thr Pro Gln Glu Pro Trp
                165                 170                 175

Pro Gly Pro Thr Ala Pro Ser Pro Thr Ser Arg Pro Pro Trp Ala Val
            180                 185                 190

Asp Pro Ala Phe Ala Glu Arg Tyr Ala Pro Asp Lys Thr Ser Thr Val
        195                 200                 205

Leu Thr Arg His Ser Gln Pro Ala Thr Pro Thr Pro Leu Gln Ser Arg
    210                 215                 220

Thr Ser Ile Val Gln Ala Ala Ala Gly Val Pro Gly Gly Gly Gly Ser
225                 230                 235                 240

Asn Asn Gly Lys Thr Pro Val Cys His Gln Cys His Lys Val Ile Arg
                245                 250                 255

Gly Arg Tyr Leu Val Ala Leu Gly His Ala Tyr His Pro Glu Glu Phe
            260                 265                 270

Val Cys Ser Gln Cys Gly Lys Val Leu Glu Glu Gly Gly Phe Phe Glu
        275                 280                 285

Glu Lys Gly Ala Ile Phe Cys Pro Pro Cys Tyr Asp Val Arg Tyr Ala
    290                 295                 300

Pro Ser Cys Ala Lys Cys Lys Lys Lys Ile Thr Gly Glu Ile Met His
305                 310                 315                 320

Ala Leu Lys Met Thr Trp His Val His Cys Phe Thr Cys Ala Ala Cys
                325                 330                 335

Lys Thr Pro Ile Arg Asn Arg Ala Phe Tyr Met Glu Glu Gly Val Pro
            340                 345                 350

Tyr Cys Glu Arg Asp Tyr Glu Lys Met Phe Gly Thr Lys Cys His Gly
```

```
              355                 360                 365

Cys Asp Phe Lys Ile Asp Ala Gly Asp Arg Phe Leu Glu Ala Leu Gly
            370                 375                 380

Phe Ser Trp His Asp Thr Cys Phe Val Cys Ala Ile Cys Gln Ile Asn
385                 390                 395                 400

Leu Glu Gly Lys Thr Phe Tyr Ser Lys Lys Asp Arg Pro Leu Cys Lys
                405                 410                 415

Ser His Ala Phe Ser His Val
            420

<210> SEQ ID NO 3
<211> LENGTH: 153
<212> TYPE: PRT
<213> ORGANISM: Homo sapiens

<400> SEQUENCE: 3

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150

<210> SEQ ID NO 4
<211> LENGTH: 223
<212> TYPE: PRT
<213> ORGANISM: Homo sapiens

<400> SEQUENCE: 4

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110
```

```
Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu His Leu Lys Lys Ser Ser Gln
                180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro
        210                 215                 220
```

<210> SEQ ID NO 5
<211> LENGTH: 53
<212> TYPE: PRT
<213> ORGANISM: Homo sapiens

<400> SEQUENCE: 5

```
Cys His Gly Cys Asp Phe Lys Ile Asp Ala Gly Asp Arg Phe Leu Glu
1               5                   10                  15

Ala Leu Gly Phe Ser Trp His Asp Thr Cys Phe Val Cys Ala Ile Cys
                20                  25                  30

Gln Ile Asn Leu Glu Gly Lys Thr Phe Tyr Ser Lys Lys Asp Arg Pro
                35                  40                  45

Leu Cys Lys Ser His
        50
```

<210> SEQ ID NO 6
<211> LENGTH: 51
<212> TYPE: PRT
<213> ORGANISM: Homo sapiens

<400> SEQUENCE: 6

```
Cys Ala Lys Cys Lys Lys Lys Ile Thr Gly Glu Ile Met His Ala Leu
1               5                   10                  15

Lys Met Thr Trp His Val His Cys Phe Thr Cys Ala Ala Cys Lys Thr
                20                  25                  30

Pro Ile Arg Asn Arg Ala Phe Tyr Met Glu Glu Gly Val Pro Tyr Cys
                35                  40                  45

Glu Arg Asp
        50
```

<210> SEQ ID NO 7
<211> LENGTH: 10
<212> TYPE: PRT
<213> ORGANISM: Homo sapiens

<400> SEQUENCE: 7

```
Gly Ala Pro Pro Pro Ala Asp Ser Ala Pro
1               5                   10
```

<210> SEQ ID NO 8
<211> LENGTH: 9
<212> TYPE: PRT
<213> ORGANISM: Artificial
<220> FEATURE:
<223> OTHER INFORMATION: a TAT domain

```
<400> SEQUENCE: 8

Arg Lys Lys Arg Arg Gln Arg Arg
1               5

<210> SEQ ID NO 9
<211> LENGTH: 16
<212> TYPE: PRT
<213> ORGANISM: Artificial
<220> FEATURE:
<223> OTHER INFORMATION: a PTD domain

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 14
<212> TYPE: PRT
<213> ORGANISM: Artificial
<220> FEATURE:
<223> OTHER INFORMATION: a PTD domain

<400> SEQUENCE: 10

Gly Arg Lys Lys Arg Arg Gln Arg Arg Arg Pro Pro Gln Cys
1               5                   10

<210> SEQ ID NO 11
<211> LENGTH: 26
<212> TYPE: PRT
<213> ORGANISM: Artificial
<220> FEATURE:
<223> OTHER INFORMATION: a PTD domain

<400> SEQUENCE: 11

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 12
<211> LENGTH: 9
<212> TYPE: PRT
<213> ORGANISM: Artificial
<220> FEATURE:
<223> OTHER INFORMATION: a PTD domain

<400> SEQUENCE: 12

Arg Arg Arg Arg Arg Arg Arg Arg Arg
1               5

<210> SEQ ID NO 13
<211> LENGTH: 12
<212> TYPE: PRT
<213> ORGANISM: Artificial
<220> FEATURE:
<223> OTHER INFORMATION: a PTD domain

<400> SEQUENCE: 13

Pro Ile Arg Arg Arg Lys Lys Leu Arg Arg Leu Lys
1               5                   10

<210> SEQ ID NO 14
<211> LENGTH: 12
<212> TYPE: PRT
<213> ORGANISM: Artificial
<220> FEATURE:
```

```
<223> OTHER INFORMATION: a PTD domain

<400> SEQUENCE: 14

Arg Arg Gln Arg Arg Thr Ser Lys Leu Met Lys Arg
1               5                   10

<210> SEQ ID NO 15
<211> LENGTH: 12
<212> TYPE: PRT
<213> ORGANISM: Artificial
<220> FEATURE:
<223> OTHER INFORMATION: a PTD domain

<400> SEQUENCE: 15

Ser Arg Arg Lys Arg Gln Arg Ser Asn Met Arg Ile
1               5                   10

<210> SEQ ID NO 16
<211> LENGTH: 12
<212> TYPE: PRT
<213> ORGANISM: Artificial
<220> FEATURE:
<223> OTHER INFORMATION: a PTD domain

<400> SEQUENCE: 16

Ser Phe His Gln Phe Ala Arg Ala Thr Leu Ala Ser
1               5                   10

<210> SEQ ID NO 17
<211> LENGTH: 12
<212> TYPE: PRT
<213> ORGANISM: Artificial
<220> FEATURE:
<223> OTHER INFORMATION: a PTD domain

<400> SEQUENCE: 17

Asp Pro Ala Thr Asn Pro Gly Pro His Phe Pro Arg
1               5                   10

<210> SEQ ID NO 18
<211> LENGTH: 12
<212> TYPE: PRT
<213> ORGANISM: Artificial
<220> FEATURE:
<223> OTHER INFORMATION: a PTD domain

<400> SEQUENCE: 18

Thr Leu Pro Ser Pro Leu Ala Leu Leu Thr Val His
1               5                   10
```

METHOD FOR CHANGING CELL PHENOTYPE USING LIM MINERALIZATION PROTEINS

CROSS-REFERENCE TO RELATED APPLICATIONS

This application is a continuation-in-part of U.S. patent application Ser. No. 11/705,942, filed Feb. 14, 2007, a continuation-in-part of U.S. patent application Ser. No. 10/292, 951, filed Nov. 13, 2002, a continuation-in-part of U.S. patent application Ser. No. 10/806,915, filed Mar. 23, 2004, as well as a continuation-in-part of U.S. patent application Ser. No. 10/399,830, filed Jul. 25, 2003. U.S. application Ser. No. 10/292,951 claims the benefit under 35 U.S.C. §119(e) of U.S. Provisional Application No. 60/331,321, filed Nov. 14, 2001. U.S. application Ser. No. 10/806,915 claims the benefit under 35 U.S.C. §119(e) of U.S. Provisional Application No. 60/456,551, filed Mar. 24, 2003, and is a continuation-in-part of U.S. application Ser. No. 09/959,578, filed Jun. 21, 2002, now issued as U.S. Pat. No. 7,045,614, which is a national stage under 35 U.S.C. §371(c) of International Application No. PCT/US2000/011664, filed Apr. 28, 2000, which in turn claims benefit under 35 U.S.C. §119(e) of U.S. Provisional Application No. 60/132,021, filed Apr. 30, 1999. U.S. application Ser. No. 10/399,830 is a national stage under 35 U.S.C. §371(c) of International Application No. PCT/US2001/046044, filed Oct. 24, 2001, which in turn claims the benefit under 35 U.S.C. §119(e) of U.S. Provisional Application No. 60/242,794, filed Oct. 24, 2000.

FIELD OF THE INVENTION

The present invention relates to use of intracellular factors for the regulation of tissue growth. More particularly, the present invention relates to the application of LIM mineralization proteins to effect cells' functions or characteristics.

BACKGROUND OF THE INVENTION

Humans and other mammalian species are prone to diseases or injuries that require tissue repair or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would result in systemic formation of new bone. Such treatment regimens would reduce the incidence of fractures arising from the loss of bone mass that is a characteristic of this disease.

In addition to diseases of the bone, soft tissue diseases, such as intervertebral disc degeneration, may be relieved or reversed by new tissue generation. Disc degeneration is associated with a progressive loss of proteoglycan matrix. This makes the disc more susceptible to further injury and causes low back pain and disc herniations. A person suffering from this condition would benefit from treatment regimen that would induce cells to increase the formation of proteoglycan cartilage.

For at least these reasons, extracellular factors have been investigated for the purpose of using them to stimulate production of new bone, proteoglycan matrix or any other tissues in need of repair. Despite the early successes achieved with extracellular signaling molecules, their use entails a number of disadvantages. For example, relatively large doses of purified extracellular proteins may be required to enhance the production of new bone, thereby increasing the expense of such treatment methods. Furthermore, they are also susceptible to degradation following their introduction into a host animal. In addition, because they are typically immunogenic, the possibility of stimulating an immune response to the administered proteins is ever present.

Due to such concerns, it would be desirable to have available treatment regimens that use intracellular signaling molecules to induce new tissue formation or regeneration.

SUMMARY

A method of changing a phenotype of a cell is provided. The method comprises increasing an amount of an amino acid sequence which is at least 70% identical to an amino acid sequence encoding an LMP protein or a fragment thereof in the cell.

The cells may be contacted by either a composition comprising a nucleic acid sequence encoding the amino acid sequence which is at least 70% identical to the amino acid sequence encoding an LMP or its fragment (e.g., SEQ ID NOs: 1-7) or by a composition comprising a nucleic acid sequence which is at least 70% identical to the amino acid sequence encoding an LMP or its fragment or any combination thereof (e.g., a nucleic acid sequence encoding amino acids of SEQ ID NOs: 1-7). The compositions may be in a sustained release formulation.

In one aspect, the cell may be contacted in vivo. The compositions may be delivered via a catheter or from an implant.

In another aspect, the cells may be transfected ex vivo. The transfected cells may be delivered to the patient from an implant or by injection.

In one aspect, the cell changes at least one of its shape, electrical activity, contractility, migration, attachment or division rate due to increase in the amount of the amino acid sequence which is at least 70% identical to the amino acid sequence encoding the LMP protein or fragments thereof.

In another aspect, the cell changes its gene expression pattern due to increase in the amount of the amino acid sequence which is at least 70% identical to the amino acid sequence encoding the LMP protein or fragments thereof.

The cells comprise non-osseous and a non-osteochondral cells. They may include differentiated, non-differentiated, and stem cells and may be selected from the group consisting of kidney cells, cardiac cells, smooth muscle cells, striated muscle cells, osteoblasts, osteoclasts, cartilage cells, endothelial cells, dental pulp cells, ligament cells, tendon cells, neural cells, nucleus pulposus cells, annulus fibrosus cells, and any combination thereof.

The target genes are genes responsible for production of molecules selected from the group consisting of BMP 2, BMP 4, BMP 6, BMP 7, BMP 12, BMP 13, Type I collagen, Type II collagen, Type III collagen, proteoglycan, aminoglycan, TGF-beta, IGF, VEGF, SMADS, ERKS, inflammatory molecules, NK-kBs, or any combinations thereof.

One aspect of this invention involves a method of changing a phenotype of a cell by contacting the cell with a pharmaceutical composition wherein the cell is non-osseous, and non-osteochondral. This pharmaceutical composition can optionally be an amino acid composition that contains one or more of the following polypeptides: LMP-1 (SEQ ID NO: 1), a polypeptide that is at least 70% identical to LMP-1, LMP-2 (SEQ ID NO: 2), a polypeptide that is at least 70% identical to LMP-2, LMP-3 (SEQ ID NO: 3), a polypeptide that is at least 70% identical to LMP-3, LMP-1s (SEQ ID NO: 4), a polypeptide that is at least 70% identical to LMP-1s, SEQ ID NO: 5, a polypeptide that is at least 70% identical to SEQ ID NO: 5, SEQ ID NO: 6, a polypeptide that is at least 70% identical to SEQ ID NO: 6, SEQ ID NO: 7, and a polypeptide that is at least 70% identical to SEQ ID NO: 7. The pharmaceutical composition can also optionally be a nucleotide composition that contains one or more polynucleotides which encode the above mentioned amino acid sequences. Furthermore, the pharmaceutical composition may contain a combination of the above mentioned amino acid compositions and the above mentioned nucleotide compositions.

For this invention, one can optionally change the phenotype of a differentiated cell, a non-differentiated cell, or a de-differentiated cell. This change of phenotype can range from a change in the cell's gene expression pattern, shape, electrical activity, contractility, migration, attachment, division rate, or a combination thereof.

In one embodiment of this invention, one changes a cell's gene expression pattern by contacting the cell with the above described pharmaceutical composition. The change in the cell's gene expression pattern is an induction of expression of a target gene, such as but not limited to BMP 2 genes, BMP 4 genes, BMP 6 genes, BMP 7 genes, BMP 12 genes, BMP 13 genes, type I collagen genes, type II collagen genes, type III collagen genes, proteoglycan genes, aminoglycan genes, TGF-beta genes, IGF genes, VEGF genes or any combination thereof.

In an alternative embodiment, the change in a cell's gene expression pattern is a repression of expression of a target gene such as but not limited to NF-κB, inflammatory molecule genes, SMADs, ERKs, and any combinations thereof.

In the method of this invention, one can change the phenotype of one or more cells such as but not limited to kidney cells, liver cells, pancreas cells, cardiac cells, smooth muscle cells, striated muscle cells, endothelial cells, dental pulp cells, ligament cells, tendon cells, neural cells, nucleus pulposus cells, annulus fibrosis cells, and any combination thereof.

In another embodiment one can change the phenotype of one or more stem cells.

In certain embodiments of this invention, the pharmaceutical composition contains polynucleotides. These polynucleotides can be included within a vector. In some embodiments, the vector is a viral vector. In other embodiments, the vector is an expression vector or a plasmid.

In some embodiments of this invention, the pharmaceutical composition contains one or more polypeptides that are cell penetrating peptides. Non-limiting examples of cell penetrating peptides include a TAT (SEQ. ID. NO. 8) or a PTD domain (SEQ. ID. NOs 9-18). In those embodiments of the invention where the pharmaceutical composition contains polynucleotides, the polynucleotides can encode one or more cell penetrating peptides.

In one embodiment of this invention, the cell being contacted with the pharmaceutical composition can be in-vivo. In this embodiment, the pharmaceutical composition can be delivered via a catheter. Alternatively, the pharmaceutical composition is in an implant or a carrier which can be positioned in an area adjacent to the cell. In these embodiments, the implant or carrier can be injectable, solid, moldable, structural or any combination thereof. The implant or carrier can be made from natural polymers, synthetic polymers, or a combination thereof. Non-limiting examples of polymers for this embodiment include collagen, collagen-ceramic combinations, BCP, DBM, PRP, MC, elastin, silk, fibrin, hyaluronic acid, chitosan, PLA, PGA, PLGA, polyorthoesters, polycaprolactone, polypropylene fumarate, polyvinyl alcohol, polyesters, polyethers, polyhydroxyls, hydrogels, or a combination thereof. The implant or carrier can include but is not limited to a bone implant, a cartilage implant, an intervertebral disc implant, a ligament implant, a tendon implant, a meniscus implant, a heart implant, a brain implant, a vascular stent, a urethral stent, and any combination thereof.

In an alternative embodiment, the cell is being contacted with the pharmaceutical composition of this invention ex-vivo. In this embodiment, the cell can be included within an implant or carrier. When the cell is within an implant or carrier, one may optionally position the implant or carrier in a desired area within the patient.

In one embodiment of this invention, the pharmaceutical composition is in a sustained-release formulation.

In another embodiment, this invention includes an implant containing a pharmaceutical composition which can optionally be an amino acid composition that contains one or more of the following polypeptides: LMP-1 (SEQ ID NO: 1), a polypeptide that is at least 70% identical to LMP-1, LMP-2 (SEQ ID NO: 2), a polypeptide that is at least 70% identical to LMP-2, LMP-3 (SEQ ID NO: 3), a polypeptide that is at least 70% identical to LMP-3, LMP-1s (SEQ ID NO: 4), a polypeptide that is at least 70% identical to LMP-1s, SEQ ID NO: 5, a polypeptide that is at least 70% identical to SEQ ID NO: 5, SEQ ID NO: 6, a polypeptide that is at least 70% identical to SEQ ID NO: 6, SEQ ID NO: 7, and a polypeptide that is at least 70% identical to SEQ ID NO: 7. In other embodiments, the pharmaceutical composition can optionally be a nucleotide composition that contains one or more polynucleotides which encode the above mentioned amino acid sequences. Furthermore, the pharmaceutical composition may also contain a combination of the above mentioned amino acid compositions and the above mentioned nucleotide compositions.

In some embodiments, the implant contains the pharmaceutical composition within a cell. In some embodiments, the implant is injectable, solid, moldable, structural or any combination thereof.

DEFINITIONS

For the purposes of better explaining the instant invention, the following non-limiting definitions are provided:

The phrase "changing gene expression pattern" refers to expressing genes which were not expressed previously; and also to significantly upregulating, downregulating or silencing expression of genes which are currently expressed.

The term "gene" refers to a DNA sequence that comprises control and coding sequences necessary for the production of a polypeptide or its precursor. The polypeptide can be encoded by a full length coding sequence (either genomic DNA or cDNA) or by any portion of the coding sequence so long as the desired activity is retained. In some aspects, the term "gene" also refers to an mRNA sequence or a portion thereof that directly codes for a polypeptide or its precursor.

The term "promoter element" or "promoter" refers to a DNA regulatory region capable of binding an RNA polymerase in a cell (e.g., directly or through other promoter-bound proteins or substances) and initiating transcription of a coding sequence.

The term "promoter sequence" is a region that is in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The term "vector" refers to a nucleic acid assembly capable of transferring gene sequences to cells (e.g., viral vectors, non-viral vectors, particulate carriers, and liposomes).

The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector.

The terms, "vector construct," "expression vector," and "gene transfer vector," generally refer to any nucleic acid construct capable of directing the expression of a gene of interest and which can transfer gene sequences to cells. Thus, the term includes cloning and expression vehicles, as well as viral vectors.

The term "antibody" refers to a whole antibody, both polyclonal and monoclonal, or a fragment thereof, for example a $F(ab)_2$, Fab, FV, VH or VK fragment, a single chain antibody, a multimeric monospecific antibody or fragment thereof, or a bi- or multi-specific antibody or fragment thereof. The term also includes humanized and chimeric antibodies.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient. In this instant, treatment involves use of this invention as a single delivery therapeutic, or multiple or repeated delivery therapeutic, or a control delivery therapeutic and is meant to be delivered locally, systemically, intravascularly, intramuscularly, intraperitoneally, inside the blood-brain barrier, or via other various routes.

The term "patient" refers to a biological system to which a treatment can be administered. A biological system can include, for example, an organ, a tissue, or a multi-cellular organism. A patient can refer to a human patient or a non-human patient.

The term "at least 70% identical" when referring to an amino acid or polynucleotide sequence includes sequences that are between about 70% and about 100% identical to the reference sequence and include 71, 72, 73, 74, 75, 76, 77, 78, 79, 80, 81, 82, 83, 84, 85, 86, 87, 88, 89, 90, 91, 92, 93, 94, 95, 96, 97, 98, and 99.

DETAILED DESCRIPTION

LIM proteins are so named because they possess a characteristic structural motif known as the LIM domain. They form a diverse group, which includes transcription factors and cytoskeletal proteins. The LIM domain is a cysteine-rich structural motif composed of two special zinc fingers that are joined by a 2-amino acid spacer. Some LIM proteins have only LIM domains (LIM-only), while others contain a variety of additional functional domains.

The LIM proteins are subdivided into two major groups. The first group includes LIM-homeodomain proteins (LIM-HD), that is, proteins having both LIM domains and a homeodomain sequence. The LIM-HD proteins are encoded by a subfamily of homeobox genes in which the various homeodomains show a high degree of similarity. Example of homeodomains found in LIM-HD to date are POU domain (named after proteins Pit, Oct, and Unc), paired homeobox (PAX), and homeobox (HOX). The second group of LIM proteins are LIM-only proteins, that is proteins having only LIM domains. In addition to these two groups, LIM protein may also posses other functional domains such as kinase domains fused to the LIM domain.

LIM-HD proteins are involved in the control of cell lineage determination and the regulation of differentiation. LIM-HD proteins are responsible for formation of multiorder, homomeric or heteromeric, transcriptional regulator complexes that allow for tissue control of developmental processes. LIM-only proteins also have an important role in regulating cell differentiation and proliferation. Several genes encoding LIM-only proteins have been associated with oncogenic chromosome translations.

This invention relates to a novel LIM protein, LIM mineralization protein (LMP), and its fragments. LMP is a pluripotent molecule, which regulates or influences a number of biological processes. The different splice variants of LMP are expected to have different biological functions in mammals. They may play a role in the growth, differentiation, and/or regeneration of various tissues.

Previously, it has been shown that LMPs induce expression of one or more bone morphogenetic proteins ("BMPs") or transforming growth factor-$\beta$ ("TGF-beta"). In addition, transfecting the non-osseous cells with nucleic acid sequence encoding LMPs stimulated production of proteoglycan or collagen. Some form of LMP is expressed in muscle, tendons, ligaments, spinal cord, peripheral nerves and cartilage. One isoform of LMP, LMP-1, has been detected in adult rat kidney, heart, brain, and lung. Boden et al., *Endocrinology* 139 (12): 5125-5134 (1998).

A LIM gene (10-4/RLMP) has been isolated from stimulated rat calvarial osteoblast cultures. See U.S. Pat. No. 6,300,127. This gene has been cloned, sequenced and assayed for its ability to enhance the efficacy of bone mineralization in vitro. The protein RLMP has been found to affect the mineralization of bone matrix as well as the differentiation of cells into the osteoblast lineage. Unlike other known cytokines (e.g., BMPs), RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

The amino acid sequence of a corresponding human protein, named human LMP-1 ("LMP-1"), has also been cloned, sequenced and deduced. See U.S. Pat. No. 6,300,127. The human protein has been found to demonstrate enhanced efficacy of bone mineralization in vitro and in vivo. The sequence of LMP-1 contains a highly conserved N-terminal PDZ domain and three C-terminal LIM domains. The sequence analysis of LMP-1 predicts two putative N-glycosylatione sites.

Additionally, a truncated (short) version of LMP-1, termed LMP-1s, has been characterized. See U.S. Pat. No. 6,300,127. This short version resulted from a point mutation in one source of a cDNA clone, providing a stop codon which truncates the protein. LMP-1s has been found to be fully functional when expressed in cell culture and in vivo.

Using PCR analysis of human heart cDNA library, two alternative splice variants (referred to as LMP-2 and LMP-3) have been identified that differ from LMP-1 in a region between base pairs 325 and 444 in the nucleotide sequence encoding LMP-1. See U.S. patent application Ser. No. 09/959,578, filed Apr. 28, 2000, pending. The LMP-2 sequence has a 119 base pair deletion and an insertion of 17 base pairs in this region. Compared to LMP-1, the nucleotide sequence encoding LMP-3 has no deletions, but it does have the same 17 base pairs as LMP-2, which are inserted at position 444 in the LMP-1 sequence.

Compositions:

A method of changing a phenotype of a cell is provided. The method comprises increasing an amount of an amino acid sequence which is at least 70% identical to an amino acid sequence encoding an LMP protein or a fragment thereof in the cell. Suitable non-limiting examples of the LMP proteins include an LMP-1 protein (SEQ. ID. No. 1), an LMP-2 protein (SEQ. ID. No. 2), an LMP-3 protein (SEQ. ID. NO. 3), and an LMP-1s protein (SEQ. ID. No. 4). The LMP proteins from species other than Homo sapiens may also be used. Such sequences are publicly available from different databases, including, but not limited to, Genbank.

In one embodiment, to increase the amount of an amino acid sequence which is at least 70% identical to an amino acid sequence encoding an LMP protein or a fragment thereof in the cell, the cell may be contacted with a composition comprising a nucleic acid sequence encoding such amino acid sequence. The nucleic acid sequences for the LMP-1, LMP-2, LMP-3, and LMP-1s proteins are known in the art. Sequences of other LMP proteins, including the LMP proteins from other species are also suitable for this invention and have been previously disclosed in patent and non-patent literature, such as, for example, U.S. Pat. No. 6,300,127, incorporated herein by reference to the extent it is not inconsistent with the instant disclosure. These nuclear acid sequences are available from public and private sources, such as, for example, Genbank.

The nucleic acid sequence may be included within a vector by methods well known in the art utilizing endonuclease and ligase properties. The vector may be a plasmid such as, for example, pUC18 and pUC 19, or a virus. The virus vectors are well known in the art and include, but are not limited to, adenoviruses, adeno-associated virus, herpex simplex virus, and retroviruses. Additional examples of vectors are listed in catalogs of different manufacturers, including, without limitation, Promega Corp. (Madison, Wis.), incorporated herein by reference in its entirety. Further, the vector may contain a promoter which directs the expression of the amino acid sequence of interest from the nucleic acid sequence. Suitable promoters include, without limitation, CMV, RSV, and TK. The vector containing the nucleic acid sequence encoding the amino acid sequence of interest is later introduced to the cells.

It is also possible to deliver the nucleic acid sequence by directly injecting into an appropriate body site, a naked, that is, unencapsulated, recombinant plasmid comprising a nucleic acid sequence that encodes LMP. In this method, transfection occurs when the naked plasmid DNA is taken up, or internalized, by the cells.

Optionally, the nucleic acid sequence may comprise an additional nucleic acid sequence encoding a protein which would facilitate the translocation of the amino acid sequence of the instant invention into the nucleus of the cell. Examples of such proteins include, but are not limited to, HIV-1 Tat protein, *Drosophila* Antennapedia homeoprotein, and HSV-1 VP22. The small protein transduction domains ("PTD") from these proteins can be fused to other proteins or peptides to transport them into cells. For example, the PTD embedded in the HIV Tat protein has been shown to successfully mediate the introduction of heterologous peptides and proteins in excess of $M_r$ 100,000 into mammalian cells in vitro and in vivo. Ho, Alan et al., Cancer Research, 61, 474-477, (2001).

Other methods exist for introducing the nucleic acid sequence into the cell. Many of these methods are described in Sambrook and Russel, Molecular Cloning: A Laboratory Manual ($3^{rd}$ Edition), Cold Springs Harbor, Press, NY, 2000. Example methods include, but are not limited to, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors.

In another embodiment, the step of increasing an amount of an amino acid sequence which is at least 70% identical to an amino acid sequence encoding an LMP protein or a fragment thereof in the cell is achieved by contacting the cell with such amino acid sequence. Examples of these amino acid sequences include, but are not limited to, SEQ ID NO: 1, SEQ ID NO: 2, SEQ ID NO: 3, or SEQ ID NO: 4. Additionally, the amino acid sequence may comprise the fragment of the LMP protein, such as, for example, a LIM domain (SEQ ID NO: 5), a LIM motif (SEQ ID NO: 6) and osteogenic region (SEQ ID NO: 7) or a combination thereof. Preferably, the amino acid sequence may be selected on the basis of the nature of the cell and the nature of the desired change in phenotype of the cell.

Optionally, the amino acid sequence of the instant invention further comprises a cell penetrating peptide such as, for example, a Tat (SEQ. ID. NO. 8) or a PTD domain (SEQ. ID. NOs 9-18). In another embodiment, the amino acid sequence of the instant invention may be packaged with a composition which advances the entry of the amino acid sequence of the instant invention into the cell. For example, the amino acid sequence may be packaged with liposomes. See, e.g., U.S. Pat. Nos. 6,338,859, 5,631,018; 6,162,462; 6,475,779; 6,521, 211; and 6,443,898, Felgner, J. H., et al. (1994). *J. Biol. Chem.* 269, 2550-2561. Zelphati, O., et al. (2001). *J. Biol. Chem.* 276, 35103-35110. Cell penetrating peptides, liposomes, transfection, and electroporation are just some examples of cell penetrating means.

The kits and reagents (e.g., Pro-Ject Protein Transfection Reagent) for introducing the amino acid sequence of the instant invention may also be purchased from commercial suppliers, such as, for example, Pierce (Rockford, Ill., Catalog #89850). Additionally, the amino acid sequence may be delivered to the cells using many of the methods for delivery of the nucleic acid sequence to the cells.

Methods of Making Amino Acid and Nucleic Acid Composition:

Following well known and conventional methods, the nucleic acid sequences for administering into the cell can be prepared by ligation of nucleic acid segments that encode LMP to other nucleic acid sequences, such as cloning and/or expression vectors. The vector may be either a plasmid or viral vector. Suitable plasmid vectors include, for example, pUC18 and pUC19. Suitable viral vectors include, but are not limited to, adenoviral vectors, adeno-associated vectors and baculoviral vectors. Additional examples of vectors are listed in catalogs of different manufacturers, including, without limitation, Promega Corp. (Madison, Wis.), incorporated herein by reference in its entirety. Methods needed to construct and analyze these recombinant vectors, for example, restriction endonuclease digests, cloning protocols, mutagenesis, organic synthesis of oligonucleotides and DNA sequencing, have been described. For DNA sequencing, the dieoxyterminator method is the preferred.

Many treatises on recombinant DNA methods have been published, including Sambrook, et al., Molecular Cloning: A Laboratory Manual, $2^{nd}$ edition, Cold Spring Harbor Press, (1988), Davis. et al., Basic Methods in Molecular Biology, Elsevier (1986), and Ausubel, et al., Current Protocols in Molecular Biology, Wiley Interscience (1988). These reference manuals are specifically incorporated by reference herein.

Primer-directed amplification of DNA or cDNA is a common step in the expression of the genes. It is typically performed by polymerase chain reaction (PCR). PCR is described in U.S. Pat. No. 4,800,159 to Mullis, et al. and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from *Thermus aquaticus*, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The nucleic acid sequence encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrence of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the *E. coli* lac promoter, is also suitable for the expression of the chimeric coding sequences. Other suitable regulatable promoters include trp, tac, recA, T7 and lambda promoters.

The present invention also includes nucleic acid molecules that hybridize under standard conditions to any of the nucleic acid sequences encoding the LIM mineralization proteins disclosed above. "Standard hybridization conditions" will vary with the size of the probe, the background and the concentration of the nucleic acid reagents, as well as the type of hybridization, for example, in situ, Southern blot, or hybrization of DNA-RNA hybrids (Northern blot). The determination of "standard hybridization conditions" is within the level of skill in the art. For example, see U.S. Pat. No. 5,580,775 to Fremeau, et al., herein incorporated by reference for this purpose. See also, Southern, J. Mol. Biol., 98:503 (1975), Alwine, et al., Meth. Enzymol., 68:220 (1979), and Sambrook, et al., Molecular Cloning: A Laboratory Manual, $2^{nd}$ edition, Cold Spring Harbor Press, 7.19-7.50 (1989).

One preferred set of standard hybrization conditions involves a blot that is prehybridized at 42° C. for 2 hours in 50% formamide, 5×SSPE (150 nM NaCl, 10 mM Na $H_2PO_4$ [pH 7.4], 1 mM EDTA [pH 8.0]) 5×Denhardt's solution (20 mg Ficoll, 20 mg polyvinylpyrrolidone and 20 mg BSA per 100 ml water), 10% dextran sulphate, 1% SDS and 100 μg/ml salmon sperm DNA. A $P^{32}$-labeled cDNA probe is added, and hybridization is continued for 14 hours. Afterward, the blot is washed twice with 2×SSPE, 0.1% SDS for 20 minutes at 22° C., followed by a 1 hour wash at 65° C. in 0.1×SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only substantially identical sequences will hybridize.

A wide variety of techniques exists for manufacturing the amino acid sequences disclosed above. They can be synthesized by standard solid peptide synthesis (Barany, G. and Merrifield, R. B., The Peptides 2:1 284, Gross, E. and Meienhofer, J., Eds., Academic Press, New York) using tert-butyloxycarbonyl amino acids and phenylacetamidomethyl resins (Mitchell, A. R. et al., J. Org. Chem. 43:2845 2852 (1978)) or 9-fluorenylmethyloxycarbonyl amino acids on a polyamide support (Dryland, A. and Sheppard, R. C., J. Chem. So. Perkin Trans. I, 125 137 (1986)). Alternatively, synthetic peptides can be prepared by pepscan synthesis (Geysen, H. M. et al., J. Immunol. Methods 03:259 (1987); Proc. Natl. Acad. Sci. USA 81:3998 (1984)), Cambridge Research Biochemicals, Cambridge, U.K. or by standard liquid phase peptide synthesis.

Alternatively, the amino acid sequences may be purified from a cellular source. The suitable sources include cells which natively express peptides containing those sequences as well as artificial expression system. Such cells include, but are not limited to, osteoblasts. The purification techniques are well known in the art. These methods include, but are not limited to, immuno-affinity chromatography, affinity chromatography, protein precipitation, buffer exchange, ion exchange chromatography, hydrophobic interaction chromatography, size-exclusion chromatography, electrophoresis or combination thereof. The amino acid sequences can also be recombinantly produced following methods well known in the art. Both the recombinant DNA techniques and purification techniques are described, for example, in Biochemistry, R. H. Garrett and C. M. Grisham, Suanders College Publishing, 1995; and Molecular and Cell Biology, Third Edition, H Lodish, D. Baltimore, A. Berk, S. L. Zipursky, P. Matsudaira, J. Darnell, Scientific American Books, Inc. 1995.

In summary, the nucleic acid sequences of the LMP protein may be prepared by methods described above. They can then be inserted into a vector which may contain a promoter to direct the expression of the amino acid sequence of interest from the nucleic acid sequence. The vector containing the nucleic acid sequence encoding the amino acid sequence of interest is later introduced to host cells. The amino acid sequences used in the methods of the instant invention can be purified or partially purified from host cells, using known purification processes as described above, and cleaved if necessary. See, e.g., Biochemistry, R. H. Garrett and C. M. Grisham, Suanders College Publishing, 1995. Molecular and Cell Biology, Third Edition, H Lodish, D. Baltimore, A. Berk, S. L. Zipursky, P. Matsudaira, J. Darnell, Scientific American Books, Inc. 1995.

Cells

A variety of different cell types may be used. In one embodiment, the cells are selected from non-osseous and non-osteochondral cells and include undifferentiated, fully differentiated and de-differentiated cells. The cells may include, but are not limited to, kidney cells, cardiac cells, smooth muscle cells, striated muscle cells, osteoblasts, osteoclasts, cartilage cells, endothelial cells, dental pulp cells, ligament cells, tendon cells, neural cells (which, for the purposes of this invention, include, without limitations, different types of neurons, neuroprogenitor cells and glial cells), nucleus pulposus cells, annulus fibrosus cells, and any combination thereof. These cells are readily available from accessible sources or may be harvested from human donors with minimal morbidity.

A person of ordinary skill in the art will recognize that in one embodiment, the change in a phenotype of the cell (e.g., a stem cell) will lead to the differentiation of the cell into a cell of an organ. Therefore, in one embodiment, the invention provides a method of generating an organ cell from a stem cell comprising increasing an amount of an amino acid sequence selected from the group consisting of an LMP-1 protein, an LMP-2 protein, an LMP-3 protein, an LMP-1s protein, SEQ ID NO: 5, SEQ ID NO: 6, SEQ ID NO: 7 or combination thereof in the stem cell. In different exemplary embodiments, the organ is a kidney, liver, pancreas, a nervous system, a heart, a smooth muscle, a striated muscle, a blood vessel, a tooth, a ligament, a tendon, or a disc.

In another embodiment, the cell may include pluripotent, multipotent, or unipotent stem cells. These stem cells may be derived from various tissue sources including, but not limited to, adipose tissue, muscle tissue, peripheral blood, cord blood, blood vessels, skeletal muscle, skin, liver and heart. The tissue may be harvested from a living donor or a cadaver.

While in a preferred embodiment the cells are derived from an autogeneic or, more preferably, an allogeneic source, the cells may also be selected from a xenogeneic source. The xenogeneic source is preferably an animal which is closely related to humans, such as a primate, or more preferably, a member of family Hominidae, such as gorilla or chimpanzee. The choice of a non-human source for the cell is advantageous because it is possible to produce a large quantity of the cells of desired type from both embryos and adult animals without legal, ethical, economic, and other concerns accompanying the use of human embryos or adults as the source of the cells.

Increasing an amount of an amino acid sequence which is at least 70% identical to an amino acid sequence encoding an LMP protein or a fragment thereof in the cell (e.g., SEQ ID NOs: 1-7 or any combination thereof) causes these cells to change their phenotype and to develop into the desired cell type, such as for example, kidney cells, pancreas cells, liver cells, neural cells, cardiac cells, smooth muscle cells, striated muscle cells, nucleus pulposus cells, annulus fibrosus cells, chondroblasts, ligament cells, tendon cells, meniscus cells, or synovial cells. The development of the cell may be verified by assessing a change in one or more of its characteristics. Such characteristics include, without limitations, changes in gene expression pattern, morphology, electrical activity, contractility, migration, attachment, or division rate. Depending on the type of the cell, a person of the ordinary skill of the art may pick the characteristic to verify that the cell reached is on its way to reaching the desired phenotype. For example, neural cells have a specific electrical activity, morphology, and markers (e.g., a microtubule-associated protein 2, β-III tubulin and NFM are examples of markers of neuronal differentiation; PSA-NCAM is a surface protein expressed on migratory neuroblasts, S100-β (15%) is the astrocyte-specific protein GFAP and vimentin are the astrocyte intermediate filament proteins. See Soltani et al, *Am J Pathol.* 2005 June; 166(6):1841-50; Deng et al, *Stem Cells* 2006 April; 24(4): 1054-64). Kidney cells have specific morphology and express specific markers (e.g., nephrin), intervertebral disc cells express aminoglycans, proteoglycans (e.g., aggrecan, versican, lumican), and collagens, calponin is expressed specifically in smooth muscle cells (Espinosa et al, *Vet Pathol.* 2002 March; 39(2):247-56), etc.

Further, the cell may change its gene pattern expression. Preferably, the cell expresses and secretes an increased amount of growth factors, such as, for example, BMP2 protein, a BMP4 protein, a BMP6 protein, a BMP7 protein, a BMP12 protein, a BMP13 protein, type I collagen, type II collagen, type III collagen, proteoglycan, aminoglycan, transforming growth factor-beta ("TGF-beta"), insulin growth factor ("IGF"), vascular endothelial growth factor ("VEGF") or any combination thereof. Alternatively, it may be desirable to repress the expression of genes which encodes a protein increasing catabolic activity of the cell. Non-limiting examples of such proteins include groups of NF-kappa-B proteins, SMADs, ERKs, inflammatory molecules, and any combination thereof. In other embodiments, where bone growth is undesirable, the repressed genes include BMPs, or other growth factors or collagens.

The changes of the one or more characteristic of the cell may be verified by a plurality of methods. For example, the change of morphology may be verified by microscopy. The changes in the division rate may be verified by [$^3$H]-thymidine incorporation assay. The changes of the gene expression pattern may be verified on the level of the mRNA of the target gene by Northern blot or quantitative RT-PCR or real-time RT-PCR. The PCR-based techniques above may be performed by methods and kits available from commercial suppliers, including, without limitations, Ambion® (Austin, Tex.). The nucleic acid sequences for the target genes are available on Genbank, and the process of selection suitable primers and the hybridization probes are well within the skill of a person of the ordinary skill in the art. The changes on the protein level may be verified, for example, by immunocytochemistry or ELISA. The antibodies against these target genes may be obtained from commercial suppliers, such as, for example, RDI division of Fitzgerald Industries Intl. (Concord, Mass.), producing antibodies specific to individual BMP proteins, or Abcam® (Cambridge, UK). Alternatively, the antibodies to the target proteins or to the amino acid sequences described above may be created by practitioner according to methods described in, for example, U.S. application Ser. No. 10/382,844, incorporated herein by reference.

The cells may be contacted by the compositions described above either ex vivo or in vivo. If the cells are located ex vivo, contacting the cells with compositions described above is followed by reimplantation of the cells into a desired area within the patient. Optionally, after contacting the cells ex vivo with compositions described above, one can culture the cells for a period of time ex vivo prior to reimplantation of the cultured cells. One can culture the cells for any appropriate length of time, a few minutes, a hour or a few hours, a day or a few days, a week or a few weeks, or even a month or longer. The exact amount of time will depend on the usage of the cells. The culture conditions will depend on the type of cells and the desired usage of those cells. When one reimplants the treated cells or the cultured cells, the area of reimplanting depends on the condition of the patient to be treated. For example, if a patient suffers from a heart condition, the cells may be delivered to myocardium. If the cells contacted in vivo, the compositions described above are delivered to the cells.

In one embodiment, the composition of the instant invention (and/or the cells, if located ex vivo) may be delivered to the desired area via an intravenous injection, a direct injection into a location adjacent to the cell or the target area, an intraperotoneal injection, a topical application to the cell or the target area, an intradiscal injection, an intraarticular injection, an intraventricular injection, or any combination thereof. For example, in one embodiment, the cell and/or compositions may be delivered via a catheter placed adjacent within or adjacent to (e.g., within 5 cm, or within 2 cm or within 1 cm) the target area. In one embodiment, the catheter may be semi-permanently positioned in the desired area, such that the practitioner will not need to remove the catheter between the administrations in the course of treatment. Yet, after the treatment has been accomplished, the catheter may be withdrawn from the patient's body. The catheter may optionally be connected to a reservoir containing either the cells or compositions and further comprising a timer or any other mechanism to control the dose of the composition released into the desired area within the patient's body. In another embodiment, the composition may be delivered by an injection from a syringe.

In another embodiment, the composition may be incorporated within an implant, such as, for example, intervertebral disc implant, a nucleus pulposus implant, a heart implant, a brain implant, a vascular stent, a urethral stent, and any combination thereof. The carrier or the actual implant may be injectable, solid, moldable, or any structural, or other combination. It may be made of natural polymers, synthetic polymers or a combination thereof In one embodiment, especially advantageous when the cell is located in vivo, the composition may be incorporated simply by soaking the implant in the solution comprising the composition. In another embodiment, the composition may be dripped, injected, sprayed, or brushed onto the implant. When placed into the target area (e.g., within the patient's body), the implant will release the composition.

In another set of embodiments, the cells contacted ex vivo may be sorted, for example, by using a cell sorter, to increase the relative ratio of the cells of the desired phenotype. After the practitioner has a sufficient amount of such cells, he can suspend the these cells in a carrier and introduce the carrier comprising the cells to the implant. In one embodiment, the carrier comprising the cells may be dripped onto the implant while optionally being gently agitated to promote homogenous distribution of the cells throughout the carrier. A person of the ordinary skill in the art will appreciate that other methods exist to incorporate the cells of the instant invention into suitable implants.

In different embodiments, the carrier or implant are made of natural polymers, synthetic polymers or a combination thereof. Suitable carrier or implant materials are disclosed in Helm, et al. "Bone Graft Substitutes for the Promotion of Spinal Arthrodesis", *Neurosurg Focus,* 10 (4) (2001).

The natural polymers suitable for the implant include, but are not limited to, collagen, elastin, silk, hyaluronic acid, chitosan, and any combinations thereof.

The suitable non-limiting examples of synthetic biodegradable polymers include alpha-hydroxy acids, such as poly-lactic acid, polyglycolic acid, enantioners thereof, co-polymers thereof, polyorthoesters, and combinations thereof.

The suitable non-limiting examples of synthetic non-biodegradable polymers include hydrogels such as PVA, delrin, polyurethane, polyethylene, co-polymers thereof and any combinations thereof.

For example, the implant may be formed of a solid material, including, without limitation, polymethylmethacrylate, silicones, polyurethanes, polyvinyl alcohol, polyamides, aromatic polyamide, polyethers, polyester liquid crystal polymers, ionomers, poly(ethylene-co-methacrylic) acids, polybutylene terephtalate (PBT), polycarbonates, polyaminocarbonates, lactic acid, glycolic acid, lactide-co-glycolides, anhydrides, orthoesters, caprolactone, epoxy, and any combinations thereof.

In other embodiments, the implant comprises a liquid composition which solidifies in vivo e.g., upon injection into the patient's body. Suitable materials which solidify in vivo include, without limitation, polysaccharides, proteins, polyphosphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), sulphonated polymers, poly(N-vinyl-2-pyrrolidone), polyethylene glycol, polyethyleneoxide, poly(2-hydroxy ethyl methacrylate), copolymers of acrylates with N-vinyl pyrrolidone, N-vinyl lactams, and any combination thereof.

Solid rigid implants are especially suitable for bone applications. Implants which are more flexible and pliable are more suitable for use as stents or for application where rigid implants may damage the surrounding tissue (e.g., cardiac implant).

All publications cited in the specification, both patent publications and non-patent publications, are indicative of the level of skill of those reasonably skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of altering an amount of at least one proteoglycan, at least one collagen, or at least one heteropolysaccharide in an extracellular matrix of an intervertebral disc, the method comprising administering directly to a cell in the intervertebral disc a pharmaceutical composition comprising:
   (a) an amino acid composition comprising LMP-1 (SEQ ID NO: 1); or
   (b) a nucleotide composition comprising a polynucleotide encoding the amino acid sequence of LMP-1 (SEQ ID NO: 1); or
   a combination of the amino acid composition and the nucleotide composition,
   wherein the pharmaceutical composition comprises a biodegradable synthetic polymer implant.

2. The method of claim 1, wherein the cell is a differentiated cell.

3. The method of claim 1, wherein the amino acid composition further comprises a cell penetrating peptide.

4. The method of claim 1, wherein the cell is located within a patient.

5. The method of claim 1 wherein the pharmaceutical composition is administered via a catheter.

6. The method of claim 1, wherein said implant further comprises a natural polymer.

7. The method of claim 1, wherein said implant comprises at least one member of the group consisting of collagen, collagen-ceramic combination, BCP, DBM, PRP, MC, elastin, silk, fibrin, hyaluronic acid, chitosan, PLA, PGA, PLGA, polyorthoesters, polycaprolactone, polypropylene fumarate, polyvinyl alcohol, polyesters, polyethers, polyhydroxyls, hydrogels, or a combination thereof.

8. The method of claim 1, wherein the implant is selected from a group consisting of a bone implant, an intervertebral disc implant and any combination thereof.

9. The method of claim 1, wherein the cell is located outside of a patient.

10. The method of claim 1, wherein the cell is a stem cell.

11. The method of claim 9, wherein the cell is included within an implant or carrier.

12. The method of claim 11 further comprising positioning the implant or carrier in a desired area within the patient.

13. The method of claim 1, wherein the cell is a nucleus pulposus cell.

14. The method of claim 1, wherein the cell is an annulus fibrosis cell.

15. The method of claim 1, wherein the implant comprises a liquid composition which solidifies in vivo.

16. The method of claim 15, wherein the liquid composition comprises polysaccharides, proteins, polyphosphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), sulphonated polymers, poly(N-vinyl-2-pyrrolidone), polyethylene glycol, polyethyleneoxide, poly(2-hydroxy ethyl methacrylate), copolymers of acrylates with N-vinyl pyrrolidone and/or N-vinyl lactams.

17. The method of claim 1, wherein the implant comprises a solid material comprising polymethylmethacrylate, silicones, polyurethanes, polyvinyl alcohol, polyamides, aromatic polyamide, polyethers, polyester liquid crystal polymers, ionomers, poly(ethylene-co-methacrylic) acids, polybutylene terephtalate (PBT), polycarbonates, polyaminocarbonates, lactic acid, glycolic acid, lactide-co-glycolides, anhydrides, orthoesters, caprolactone and/or epoxy.

18. The method of claim 7, wherein the implant further comprises PLA, PGA, PLGA, polyorthoesters, polycaprolactone, polypropylene fumarate, polyvinyl alcohol, polyesters, polyethers, polyhydroxyls and/or hydrogels.

19. The method of claim 1, wherein the pharmaceutical composition is administered to the cell through sustained release.

* * * * *

UNITED STATES PATENT AND TRADEMARK OFFICE
CERTIFICATE OF CORRECTION

| | | |
|---|---|---|
| PATENT NO. | : 8,252,738 B2 | Page 1 of 1 |
| APPLICATION NO. | : 11/875267 | |
| DATED | : August 28, 2012 | |
| INVENTOR(S) | : Marx et al. | |

It is certified that error appears in the above-identified patent and that said Letters Patent is hereby corrected as shown below:

On the Title Page, in item (56), under "OTHER PUBLICATIONS", in Column 2, Line 33, delete "Rheumatoogy." and insert -- Rheumatology. --, therefor.

In Column 2, Line 54, delete "SMADS, ERKS" and insert -- SMAD$_S$, ERK$_S$, --, therefor.

In Column 8, Line 67, delete "Davis." and insert -- Davis, --, therefor.

In Column 13, Line 25, delete "thereof" and insert -- thereof. --, therefor.

In Column 13, Line 37, delete "the these" and insert -- these --, therefor.

In Column 26, Line 56, in Claim 5, delete "1" and insert -- 1, --, therefor.

In Column 27, Line 9, in Claim 12, delete "11" and insert -- 11, --, therefor.

Signed and Sealed this
Twenty-third Day of October, 2012

David J. Kappos
*Director of the United States Patent and Trademark Office*